(12) United States Patent
Schlenker et al.

(10) Patent No.: US 9,004,451 B2
(45) Date of Patent: Apr. 14, 2015

(54) CONROL VALVE FOR A MEDICAL SUCTION DEVICE

(75) Inventors: Stefan Schlenker, Freiburg (DE); Thomas Lietzau, Freiburg (DE); Hartmund Biedermann, Denzlingen (DE)

(73) Assignee: Schölly Fiberoptic GmbH, Denzlingen (DE)

(*) Notice: Subject to any disclaimer, the term of this patent is extended or adjusted under 35 U.S.C. 154(b) by 320 days.

(21) Appl. No.: 13/363,637

(22) Filed: Feb. 1, 2012

(65) Prior Publication Data

US 2012/0211104 A1 Aug. 23, 2012

(30) Foreign Application Priority Data

Feb. 17, 2011 (DE) .......................... 10 2011 011 399

(51) Int. Cl.
*F16K 1/00* (2006.01)
*A61M 39/22* (2006.01)
*A61M 1/00* (2006.01)

(52) U.S. Cl.
CPC ............. *A61M 39/22* (2013.01); *A61M 1/0041* (2013.01)

(58) Field of Classification Search
USPC .......... 251/318–319, 320; 604/27–30, 34–35, 604/118–119, 149, 156, 167.03, 132–133, 604/129, 33; 128/207.14–207.16; 600/158–159
See application file for complete search history.

(56) References Cited

U.S. PATENT DOCUMENTS 4,562,830 A * 1/1986 Yabe .............................. 600/155
5,013,300 A * 5/1991 Williams ....................... 604/119
6,331,172 B1 * 12/2001 Epstein et al. .................. 604/82

* cited by examiner

*Primary Examiner* — Marina Tietjen
(74) *Attorney, Agent, or Firm* — Volpe and Koeing, P.C.

(57) ABSTRACT

A control valve (8) for a medical suction device (1) is provided, with the control valve (8) having an actuating element for freeing and closing a flow path (15) through a valve chamber (11) through the use of a valve plunger (12). Additional air intake openings (16) are formed on the actuating element (10) and define an additional flow path (21) through the valve chamber (11).

11 Claims, 4 Drawing Sheets

CONROL VALVE FOR A MEDICAL SUCTION DEVICE

CROSS-REFERENCE TO RELATED APPLCIATIONS

This application claims the benefit of German Patent Applciation No. 10 2011 011 399.1, filed Feb. 17, 2011, which is incorporated herein by reference as if fully set forth.

BACKGROUND

The invention relates to a control valve for a medical suction device, in particular for a bronchoscope, said control valve having an actuating element connected to a valve plunger movable in a valve chamber.

Control valves of this kind are known and are used to connect or interrupt the suction stream of the suction device in a simple manner, without a suction pump having to be turned on or off.

For many medical uses, it is desirable to regulate the strength of the suction stream, since strong suction is sometimes desired, and sometimes only weak suction is needed.

In the known control valves, this can be achieved by the valve plunger being moved out of a valve seat to a greater or lesser extent. This is typically done by hand. A disadvantage of this method is that a careless movement can cause the suction stream to suddenly vary in an uncontrolled manner.

SUMMARY

The object of the invention is to improve the performance characteristics of a control valve.

In a control valve of the type mentioned at the outset, this object is achieved, according to the invention, in that at least one air intake opening, which is open to the outside, is formed on the actuating element and leads into the valve chamber. An advantage of this is that the air intake opening affords an additional possibility of regulating the strength of the suction stream, with the air intake opening being able to be closed for a strong suction stream and being able to be freed or opened for a weak suction stream. Thus, the person using the control valve according to the invention no longer has to ensure that the valve plunger is in a defined intermediate position between a completely opened control valve and a completely closed control valve in order to obtain a desired suction stream. Instead, the user can set the desired strength of the suction stream by simply opening or closing the air intake opening(s).

For simple handling of the control valve, it can be provided that a finger support surface for manual actuation of the valve plunger is formed on the actuating element.

In one embodiment of the invention, it can be provided that the at least one air intake opening is formed in a finger support surface or the finger support surface. An advantage of this is that the actuation of the valve plunger and the closure of the at least one air intake opening can be performed using the same finger. This further improves the performance characteristics of the control valve.

For good maneuverability of the actuation element, it can be provided that the finger support surface has a concave shape. Here, a surface with a concave shape is understood as an inwardly curved surface, for example of the kind found in the reflective surface of a concave mirror. The concave shape has the advantage of largely avoiding the possibility of the finger slipping from the finger support surface and, consequently, from the actuating element.

To permit finer regulation of the strength of the suction stream, it can be provided that at least two air intake openings, in particular more than two air intake openings, or several air intake openings, which each lead into the valve chambers, are formed on the actuating element. An advantage of this is that, by closing one air intake opening or two air intake openings or three or more air intake openings, the user is able to vary in fine steps the cross section of the air inlet defined by the opened air intake openings.

It is particularly favorable for manual actuation if the air intake openings are formed in a finger support surface or the finger support surface.

According to one embodiment of the invention, it can be provided that the air intake openings are arranged on a circle and/or about a circle center point. An advantage of this is that the rotationally symmetrical arrangement of the air intake openings permits intuitive use without complicated visual monitoring. The user is able to close the number of air intake openings that he wishes to close, without checking the spatial orientation in which the control valve is located at the time. He is thus able to rely on the sense of touch afforded him by the actuating element.

In one embodiment of the invention, it can be provided that the at least one air intake opening leads into the valve chamber at a position which, in the suction direction, lies ahead of a valve seat. An advantage of this is that the flow path can be completely closed by the valve plunger. A further advantage is that, with the control valve closed, the air intake openings are able to relieve the pump-side connection hoses when the pump is running.

For complete interruption of the flow path at the distal end of the suction device, it can be provided that the valve plunger is arranged movably between an open position and a closed position.

It can be provided that a flow path formed between a valve inlet and a hose or tube connection can be freed and closed by the valve plunger.

For regulating the strength of the suction stream, it can be provided that the at least one air intake opening can be opened or freed at least in the open position of the valve plunger. It is in this way possible to ensure that, with the valve plunger opened and the air intake opening opened, the running pump partially sucks air through the air intake opening, which leads to a reduction in the strength of the suction stream at the distal end of the medical suction device.

In a sturdy embodiment of the invention, it can be provided that the actuating element and the valve plunger are integrally connected. In this case, the actuating element and the valve plunger can be produced, for example cast or turned, from one piece.

It can be provided that the actuating element is formed in a plate shape or disk shape on one end of the valve plunger. An advantage of this is that a wall area of the valve chamber can be formed by the actuating element.

It can be provided that the air intake opening(s) is (are) formed as through-bore(s) in the actuating element. An advantage of this is that the air intake openings can be easily formed on the actuating element in a small number of production steps.

In one embodiment of the invention, it can be provided that the valve chamber has an elastic, annular wall portion, which is fitted between the actuating element and a valve body that receives the valve plunger. An advantage of this is that the wall portion can apply the restoring force needed to bring the valve plunger into the closed position. It is possible to dispense with additional restoring springs.

The invention thus also relates to a medical suction device with a control valve according to the invention. The control valve is preferably connected releasably to a main body of the suction device.

BRIEF DESCRIPTION OF THE DRAWINGS

The invention will now be described in more detail on the basis of an illustrative embodiment, although it is not limited to this illustrative embodiment. Further illustrative embodiments are obtained by combination of one or more features of the claims and/or one or more features of the illustrative embodiment.

In the drawing.

DETAILED DESCRIPTION FO THE PREFERRED EMBODIMENTS

Figure 1:
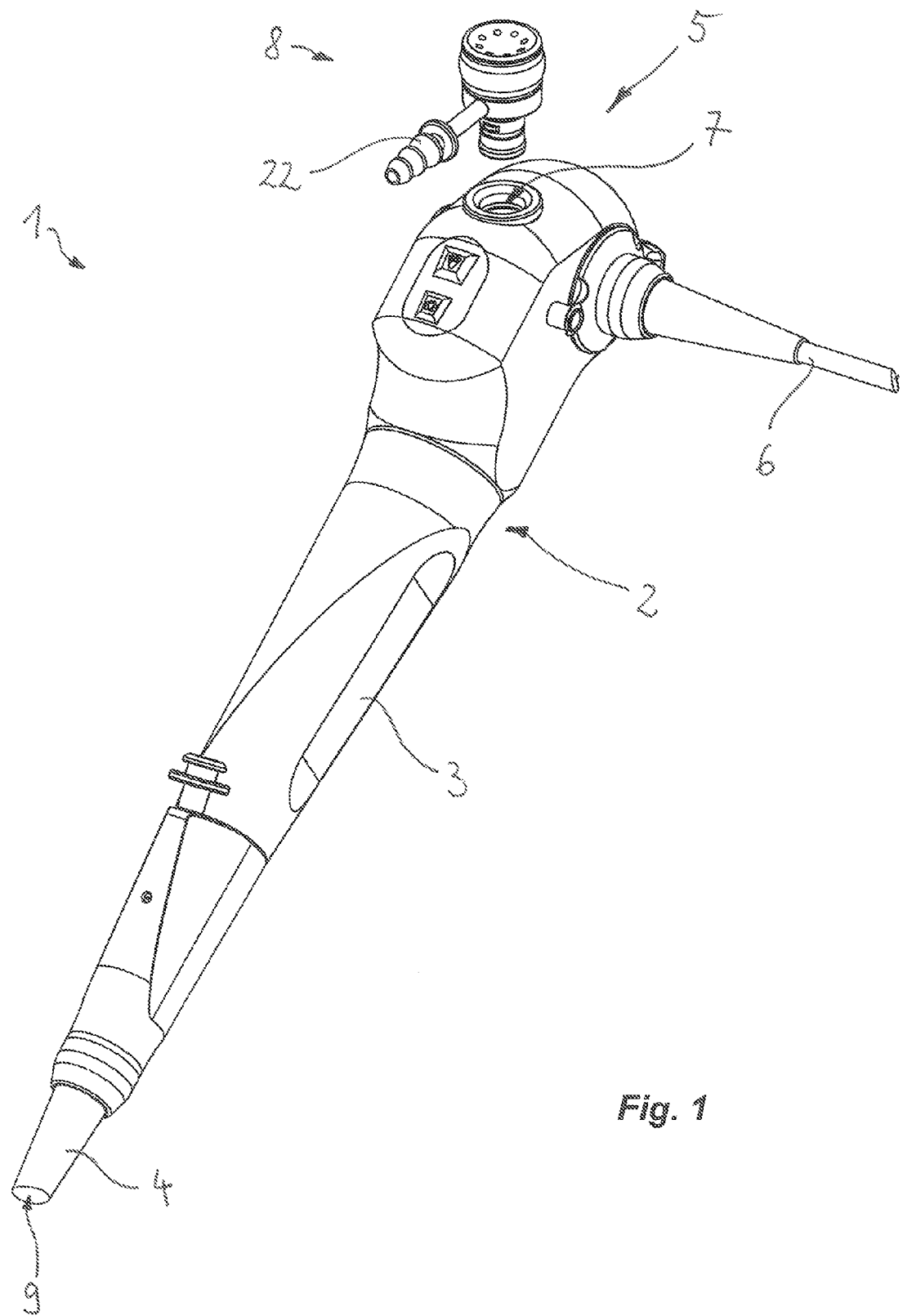
FIG. 1 shows a three-dimensional perspective view of a medical suction device with a control valve according to the invention.

A medical suction device, designated as a whole by reference number 1 in FIG. 1, has a main body 2 with a grip 3 formed on the latter.

FIG. 1 shows a bronchoscope for illustrating the invention.

A connection cable 6 through which electrical and/or optical signals can pass is formed at the end of the main body 2 directed toward the user, i.e. at the proximal end.

The main body 2 also has a control head 5, on which a distal hose 4 of the medical suction device 1 is secured. The distal hose 4 has, among other things, a suction channel 9 designed in a manner known per se.

In order to connect the suction channel 9 to a pump (not shown), a control valve 8 is fitted in a valve seat 7 on the control head 5.

Figure 2:
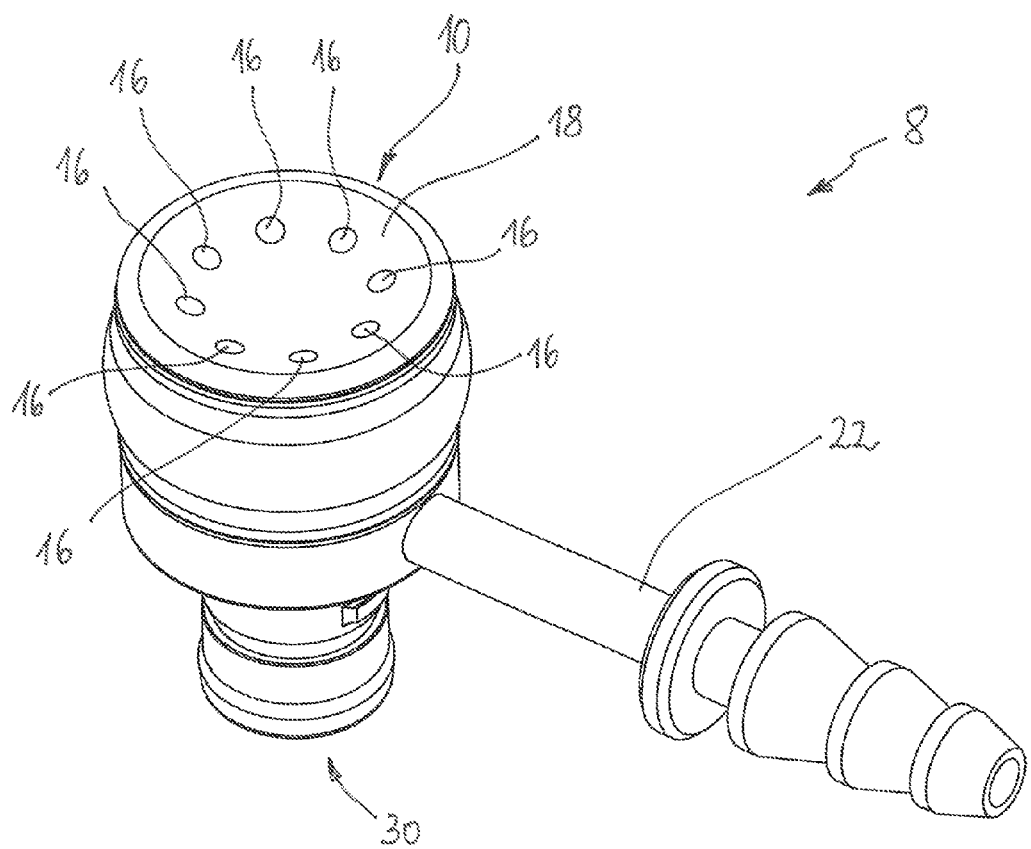
FIG. 2 shows the control valve according to the invention from FIG. 1 in a three-dimensional perspective view from above.
Figure 3:
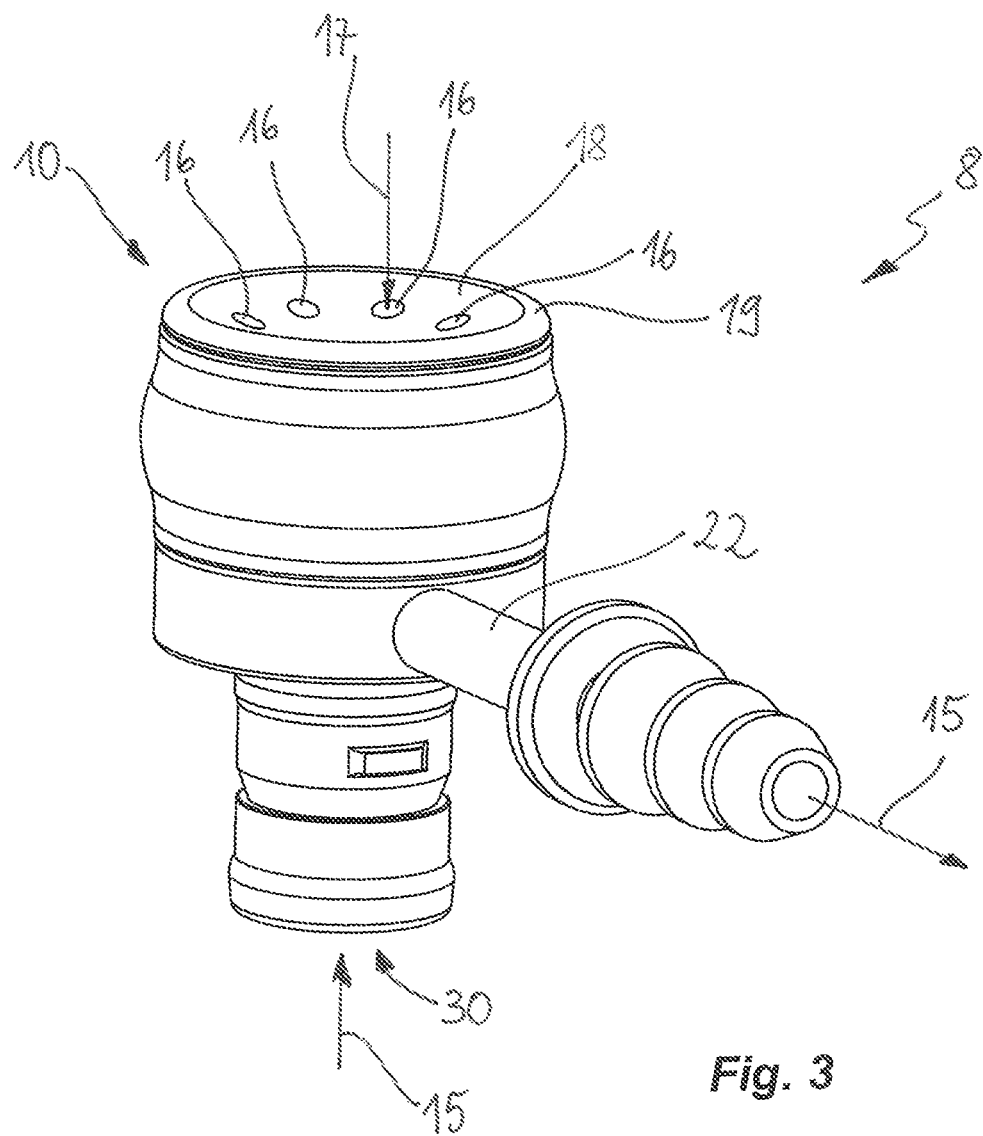
FIG. 3 shows the control valve according to the invention from FIG. 2 in a perspective view from the side.
Figure 4:
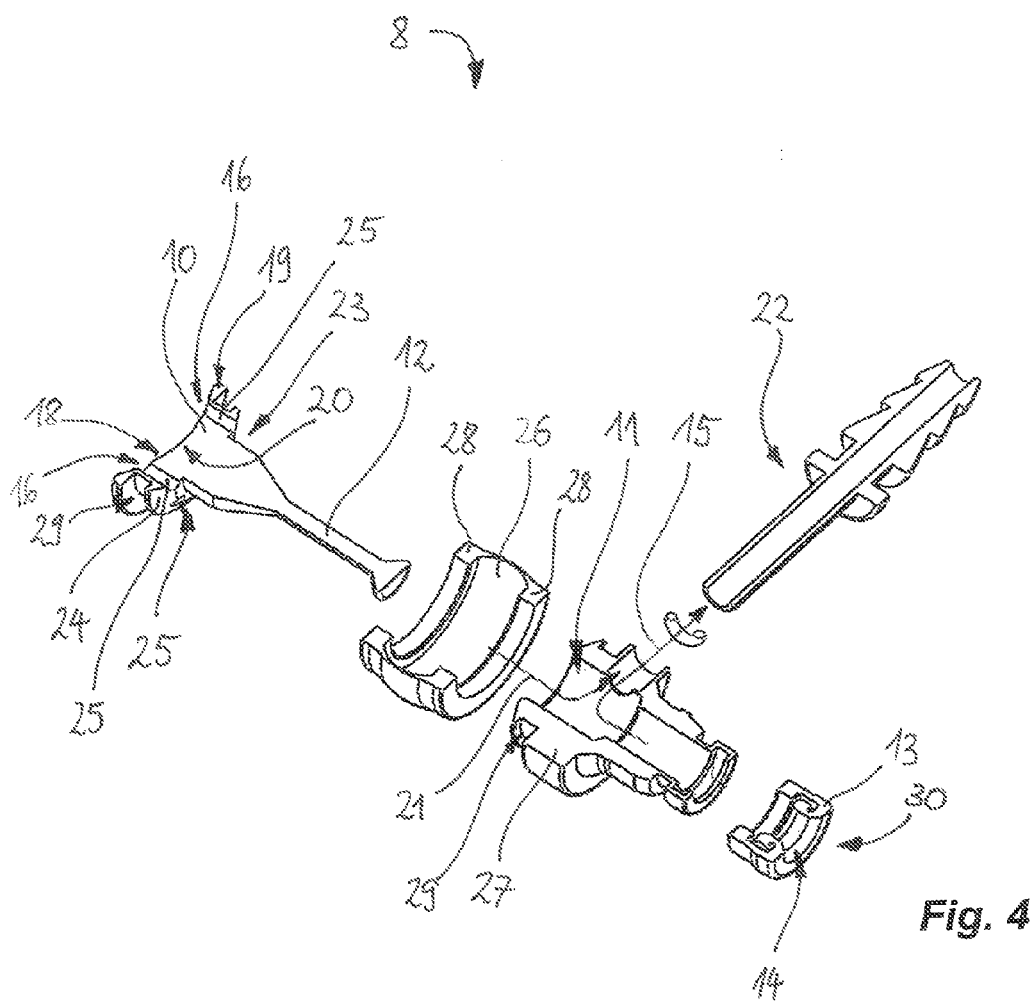
FIG. 4 shows an exploded and cross-sectional view of the control valve according to the invention from FIG. 1.

The control valve 8 is shown in detail in FIGS. 2 to 4.

The control valve 8 has an actuating element 10, with which a valve chamber 11 of the control valve 8 can be freed and closed for the suction procedure.

For this purpose, the actuating element 10 is connected integrally to a valve plunger 12, which is arranged movably on the valve chamber 11 at the valve inlet 30. It will be seen from FIG. 4 that the valve plunger 12 is arranged movably in the valve chamber 11 in the assembled position.

Depending on the actuation of the actuating element 10, the valve plunger 12 thus opens or closes a valve seat 14 formed on the sealing ring 13.

The valve plunger 12 is thus movable between an open position and a closed position, with a flow path 15 being freed in the open position, and the flow path 15 being closed in the closed position.

Air intake openings 16, open to the outside, are formed on the actuating element 10 and lead into the valve chamber 11 and thus form an additional air inlet 17.

For manual actuation of the valve plunger 12, a finger support surface 18 is formed on the outside of the actuating element 10.

It will be seen from FIG. 3 and FIG. 4 that the finger support surface 18 has a concave shape in the manner of a concave mirror, with the edge 19 of the finger support surface 18 being designed and arranged higher than the center 20 of the finger support surface 18.

The air intake openings 16 are formed in the finger support surface 18 and can thus be easily closed by a finger applied to actuate the valve plunger 12.

Thus, depending on the number of the air intake openings 16 closed in this way, the suction power at the valve seat 14 can be easily varied with the valve plunger 12 opened.

In the illustrative embodiment shown, there are eight air intake openings 16 in total.

It will be seen from FIG. 2 that the air intake openings 16 are arranged on an imaginary circle, of which the center point lies at the center 20 of the finger support surface 18. The actuating element 10 can thus turn around the axis predefined by the valve plunger 12 and passing through the center 20, without this adversely affecting the performance characteristics from the point of view of the user.

In other illustrative embodiments, other numbers of air intake openings 16 can be formed, for example two air intake openings, three air intake openings, four air intake openings or more than four air intake openings.

It will be seen from FIG. 4 that an additional flow path 21 is formed through the air intake openings 16, and this additional flow path 21 combines with the flow path 15 from the suction channel 9 of the distal hose 4 in the valve chamber 11.

The air intake openings 16 thus lead into the valve chamber 11 at a position which, in the suction direction predefined by the main flow path 15, lies ahead of the valve seat 14 of the valve plunger 12. Here, ahead denotes that the suctioned medium first has to flow through the valve seat 14 before it reaches the valve chamber 11.

The main flow path 15, between the valve inlet 30 and a hose or tube connection 22, and the additional flow path 21, between the air intake openings 16 and the hose or tube connection 22, lead through the hose or tube connection 22 into the pump (not shown).

It will also be seen from FIG. 4 that the actuating element 10 is formed in a plate shape or disk shape on an end 23 of the valve plunger 12.

The actuating element 10 thus forms, on the inside, a wall area 24 of the valve chamber 11. The wall area 24 is arranged on that side of the actuating element 10 directed away from the finger support surface 18.

FIG. 4 shows through-bores 25, which are formed in the actuating element 10 for each air intake opening 16. Thus, the air intake openings 16 lead into the valve chamber 11 via these through-bores 25.

The valve chamber 11 has a wall portion 26, which is fitted and arranged between the actuating element 10 and a valve body 27.

The wall portion 26 has an annular shape and surrounds the valve plunger 12 in the radial direction with respect to the axis of the valve plunger 12.

To secure the wall portion 26 on the valve body 27, annular securing beads 28 are integrally formed on the wall portion 26 and are fitted into corresponding receiving grooves 29.

The wall portion 26 is made of an elastic material and thus has the effect of guiding and restoring the valve plunger 12.

According to the invention, in the control valve 8 for a medical suction device 1, said control valve 8 having an actuating element for freeing and closing a flow path 15 through a valve chamber 11 by means of a valve plunger 12, it is provided that additional air intake openings 16 are formed on the actuating element 10 and define an additional flow path 21 through the valve chamber 11.

The invention claimed is:

1. A control valve (8) for a medical suction device (1), the control valve (8) comprising an actuating element (10) connected to a valve plunger (12) movable in a valve chamber (11), wherein two or more air intake openings (16), which are open to atmosphere, are formed on the actuating element (10) and lead into the valve chamber (11), the two or more air intake openings are closable by a user and a cross-section of an air inlet defined by the two or more air intake openings is variable in fine steps by individually closing one or more of the air intake openings (16), a finger support surface (18) for manual actuation of the valve plunger (12) is formed on the actuating element (10), and the two or more air intake openings (16) are formed in the finger support surface (18); wherein the valve chamber (11) has an elastic, annular wall portion (26), which is fitted between the actuating element (10) and a valve body (27) that receives the valve plunger (12).

2. The control valve (8) as claimed in claim 1, wherein the finger support surface (18) has a concave shape.

3. The control valve (8) as claimed in claim 1, wherein the two or more air intake openings (16) lead into the valve chamber (11) at a position which, in a suction direction, lies ahead of a valve seat (14) of the valve plunger (12).

4. The control valve (8) as claimed in claim 1, wherein the valve plunger (12) is arranged movably between an open position and a closed position.

5. The control valve (8) as claimed in claim 1, wherein the actuating element (10) and the valve plunger (12) are integrally connected.

6. The control valve (8) as claimed in claim 1, wherein the two or more air intake openings (16) are formed as throughbores (25) in the actuating element (10).

7. The control valve (8) as claimed in claim 1, wherein the air intake openings (16) are arranged at least one of on a circle or in rotationally symmetrically about a circle center point (20).

8. The control valve (8) as claimed in claim 1, wherein a flow path (15) formed between a valve inlet (30) and a hose or tube connection (22) is freed and closed by the valve plunger (12).

9. The control valve (8) as claimed in claim 1, wherein the two or more air intake openings (16) are opened or freed at least in an open position of the valve plunger (12).

10. The control valve (8) as claimed in claim 1, wherein the actuating element (10) is formed in a plate shape or disk shape on one end (23) of the valve plunger (12).

11. A control valve (8) for a medical suction device (1), the control valve (8) comprising an actuating element (10) connected to a valve plunger (12) movable in a valve chamber (11), wherein two or more air intake openings (16), which are open to outside, are formed on the actuating element (10) and lead into the valve chamber (11), the two or more air intake openings are closable by a user and a cross-section of an air inlet defined by the two or more air intake openings is variable in fine steps by individually closing one or more of the air intake openings (16), a finger support surface (18) for manual actuation of the valve plunger (12) is formed on the actuating element (10), and the two or more air intake openings (16) are formed in the finger support surface (18); wherein the actuating element (10) forms a wall area (24) of the valve chamber (11).

* * * * *